(12) United States Patent
Patel

(10) Patent No.: US 6,673,617 B2
(45) Date of Patent: Jan. 6, 2004

(54) TEST STRIP QUALIFICATION SYSTEM

(75) Inventor: Harshad Patel, Fremont, CA (US)

(73) Assignee: Lifescan, Inc., Milpitas, CA (US)

( * ) Notice: Subject to any disclaimer, the term of this patent is extended or adjusted under 35 U.S.C. 154(b) by 0 days.

(21) Appl. No.: 10/100,531

(22) Filed: Mar. 14, 2002

(65) Prior Publication Data

US 2003/0175978 A1 Sep. 18, 2003

(51) Int. Cl.[7] .................... G01N 31/00; G01N 33/86
(52) U.S. Cl. ...................... 436/8; 436/69; 435/13; 600/369; 73/64.41; 702/19; 702/32
(58) Field of Search .................... 436/8, 63, 69, 436/180; 422/73, 100; 435/13; 600/368, 369; 73/64.41; 702/19, 31, 32

(56) References Cited

U.S. PATENT DOCUMENTS

| | | | |
|---|---|---|---|
| 5,230,866 A | | 7/1993 | Shartle et al. |
| 5,504,011 A | | 4/1996 | Gavin et al. |
| 5,591,403 A | | 1/1997 | Gavin et al. |
| 6,084,660 A | * | 7/2000 | Shartle .......................... 356/39 |
| 6,261,519 B1 | * | 7/2001 | Harding et al. ................ 422/58 |
| 6,521,182 B1 | * | 2/2003 | Shartle et al. ................ 422/58 |
| 2001/0004641 A1 | | 6/2001 | Hawkins |
| 2002/0064480 A1 | * | 5/2002 | Shartle ......................... 422/57 |
| 2002/0098114 A1 | * | 7/2002 | Harding et al. ............... 422/56 |
| 2002/0110486 A1 | * | 8/2002 | Shartle et al. ................ 422/57 |
| 2002/0110922 A1 | * | 8/2002 | Shartle et al. ............... 436/169 |
| 2003/0031594 A1 | * | 2/2003 | Shartle et al. ................ 422/58 |
| 2003/0044318 A1 | * | 3/2003 | Olson .......................... 422/58 |

FOREIGN PATENT DOCUMENTS

| | | |
|---|---|---|
| EP | 0 974 840 A2 | 7/1999 |
| EP | 0 974 840 A2 | 1/2000 |
| EP | 1069427 * | 1/2001 |
| EP | 1107004 * | 6/2001 |
| WO | WO 95/12127 | 5/1995 |
| WO | 01/75433 * | 10/2001 |

* cited by examiner

Primary Examiner—Maureen M. Wallenhorst
(74) Attorney, Agent, or Firm—Frank P. Becking; Bozicevic, Field & Francis LLP

(57) ABSTRACT

In connection with a fluidic medical diagnostic device that permits measurement of the coagulation time of blood, software, methods and associated devices for quality control are disclosed. The fluidic device preferably includes a test strip with one end having a sample port for introducing a sample and a bladder at the other end for drawing the sample to a measurement area. A channel carries sample from the sample port to an assay measurement area and first and second control measurement areas. Preferably a stop junction, between the measurement areas and bladder, halts the sample flow for measurement. If results from measurements taken for each control fall within a predetermined zone or defined limits, the assay measurement is qualified. If not, an error is registered and the test strip is counted as unfit.

17 Claims, 3 Drawing Sheets

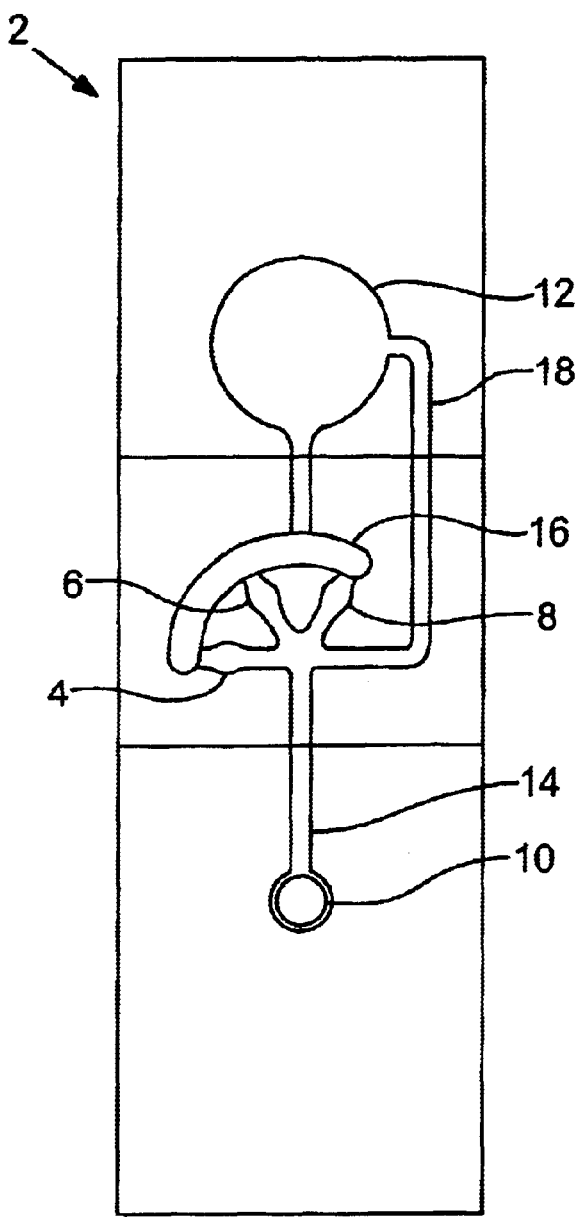
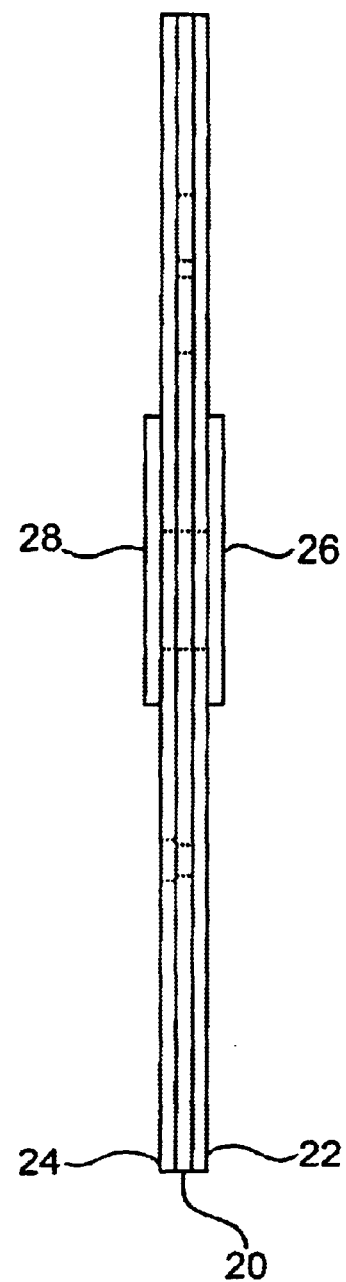
FIG. 1A
PRIOR ART
FIG. 1B
PRIOR ART

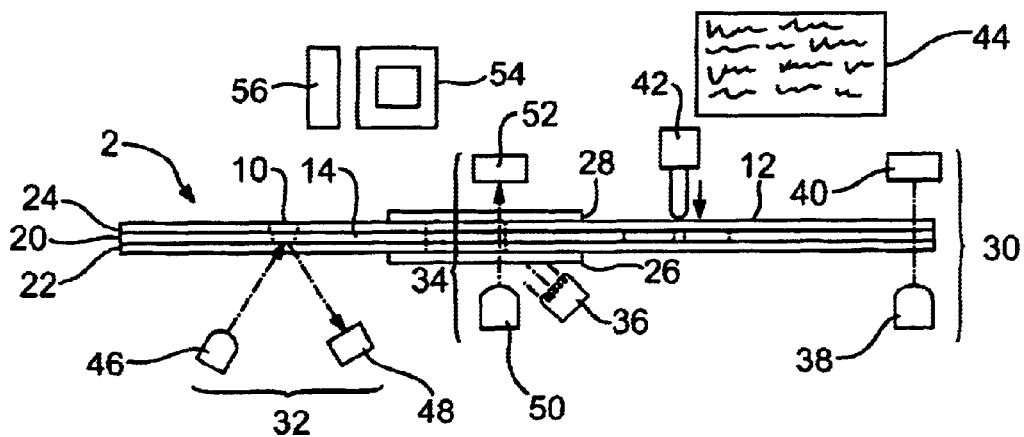
PRIOR ART FIG. 2A
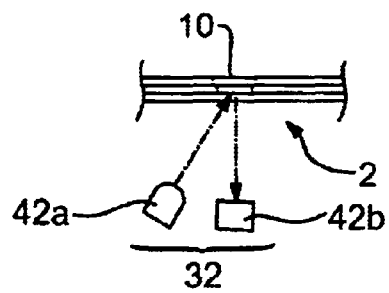
PRIOR ART FIG. 2B
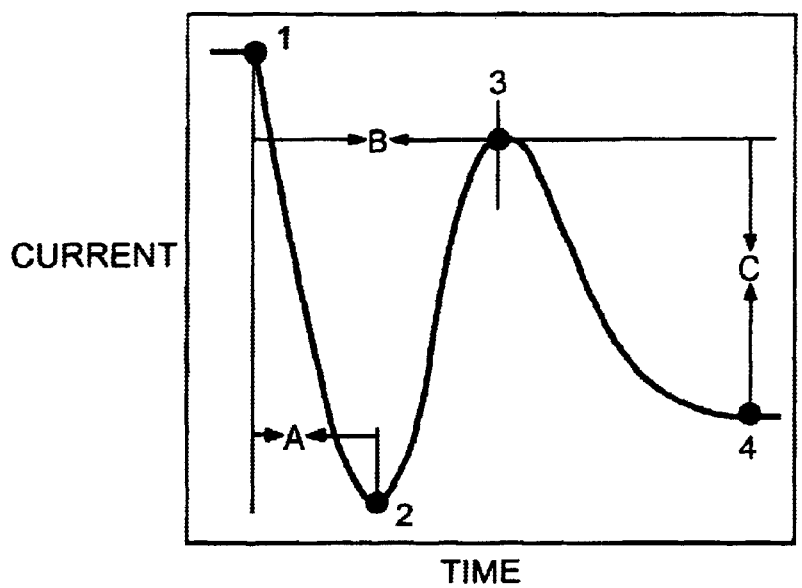
**FIG. 3
PRIOR ART**

TEST STRIP QUALIFICATION SYSTEM

FIELD OF THE INVENTION

This invention relates to approaches for qualifying results obtained in using analyte test strips. The invention is particularly suited for testing the quality of test strips used for measuring prothrombin time (PT time) with whole blood in which a measurement area includes a composition that catalyzes the blood clotting cascade.

BRIEF DESCRIPTION OF THE DRAWINGS

FIGS. 1–3 represent information known in the art and are referenced in the Background of the Invention.

FIG. 1A is a top view of a test strip as may be used in connection with the present invention; FIG. 1B is a side view of that test strip.

FIG. 2A is a schematic of hardware elements for a meter for that may be used in the present invention; FIG. 2B shows an alternative variation of an element of the meter in FIG. 2A.

FIG. 3 is a graph of data as used to determine PT time.

FIG. 4 is a graph showing a qualification zone for a first control.

FIG. 5 is a graph showing a qualification zone for a second control.

BACKGROUND OF THE INVENTION

Figure 4:
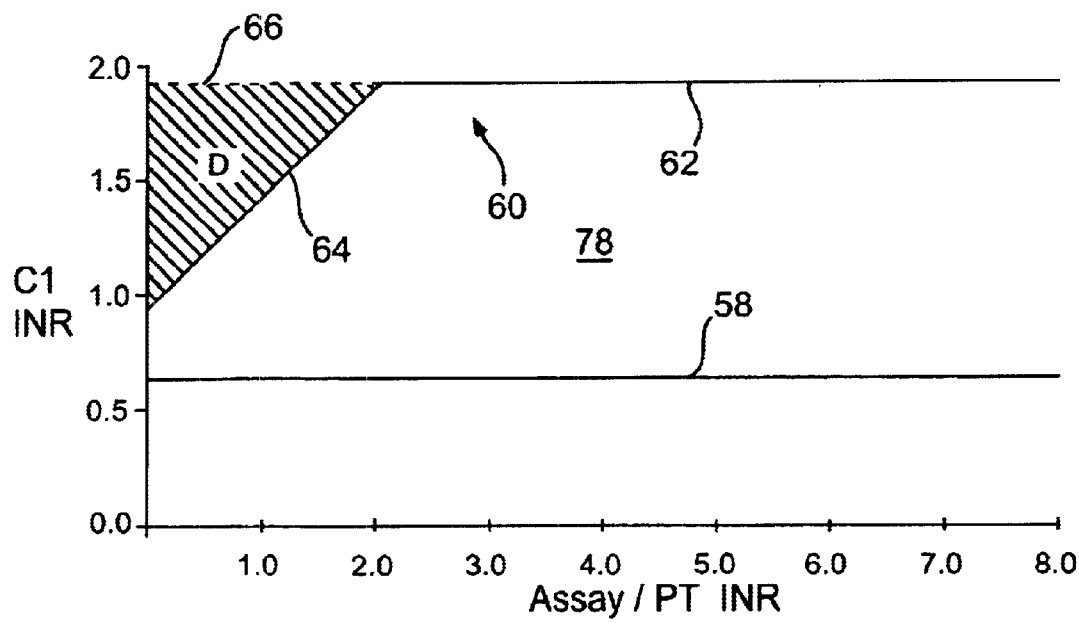
FIGS. 4 and 5 diagrammatically illustrate aspects of the present invention. Variation of the invention from that shown in the figures is contemplated.

European patent application EP 0 974 840 the ('840 publication), published Jan. 26, 2001, describes a device and system that may be used with the present invention. FIG. 1 presented herein as adapted from the 840 publication shows a parallel multi-channel test strip 2. In it, measurement areas 4, 6 and 8 are provided. Upon introducing a sample, usually whole blood, at introduction port 10 and depressing a bladder 12 and releasing it, a partial vacuum draws the blood though channel 14 up to shared stop junction 16. The test strip also includes a bypass channel 18 which draws sample toward bladder 12 to alleviate negative pressure at the stop junction order to prevent overcoming the surface tension that pins the fluid in the measurement areas at the stop junction.

For PT measurements, it is important to stop the flow of sample as it reaches that point to permit reproducible "rouleaux formation"—the stacking of red blood cells—which is an important step in monitoring blood clotting using the present invention. The principle of stop junction operation is described in U.S. Pat. No. 5,230,866.

A test strip body is described as preferably produced from three layers. The elements above are formed by cutouts in intermediate layer 20, sandwiched between a top layer 22 and bottom layer 24. Preferably, layer 22 is double-sided adhesive tape. Stop junction 16 is preferably formed by an additional cutout in layer 22 and/or 24, aligned with the cutout in layer 22 and sealed with sealing layer 26 and/or 28.

Each cutout for stop junction 16 is preferably at least as wide as channel 14. A filter may optionally be used to cover sample port 10. The filter separates red blood cells from a whole blood sample and/or may contain a reagent to interact with the blood to provide additional information. A suitable filter comprises an anisotropic membrane, preferably a polysulfone membrane of the type available from Spectral Diagnostics, Inc., (Toronto, Canada). An optional reflector may be on, or adjacent to, a surface or layer of test strip 2 and positioned over the measurement areas. If a reflector is present, the device becomes a transflectance device.

Typically, in producing the test strip, reagent is bubble-jet printed onto areas 4, 6 and 8. The chemicals at each site are disclosed in the 840 publication as: 1) thromboplastin in area 4; 2) thromboplastin bovine eluate, and recombinant Factor VIIa in area 6 and 3) thromboplastin and bovine eluate alone in area 8. The composition in area 6 is selected to normalize the clotting time of a blood sample by counteracting the effect of an anticoagulant, such as warfarin. The composition in area 8 is selected to partially overcome the effect of an anticoagulent. The bovine eluate (plasma barium citrate bovine eluate) is available from Haemotologic Technologies, (Burlington, Vt.); recombinant Factor VIIa from American Diagnostica, (Greenwich, Conn.). Thromboplastin (recombinant Tissue Factor/PT reagent), from Ortho Clinical Diagnostics, (Raritan, N.J.).

After printing, a sample port is cut in untreated polyester film such as AR1235, available from Adhesives Research, (Glen Rock, Pa.) and then laminated, in register, to the top of the double-sided tape after removing the release layer. A die then cuts the stop junction through the three layers of the sandwich. Finally, strips of single-sided adhesive tape such as MSX4841, available from 3M, (St. Paul, Minn.) are applied to the outside of the polyester layers to seal the stop junction.

Use of the test strip can be understood with reference to a schematic of the elements of a meter shown in FIGS. 2A and 2B (also adapted from the 840 publication), which contemplates an automated meter. Alternatively, manual operation is also possible. In that case, bladder 12 is manually depressed before sample is applied to port 10, then released. The first step the user performs is to turn on the meter, thereby energizing strip detector 30, sample detector 32, measurement system 34, and optional heater 36. The second step is to insert the strip. Preferably, the strip is not transparent over at least a part of its area, so that an inserted strip will block the illumination by LED 38 of detector 40. (More preferably, the intermediate layer is formed of a non-transparent material, so that background light does not enter measurement system 34.) Detector 40 thereby senses that a strip has been inserted and triggers bladder actuator 42 to compress bladder 12. A meter display 44 then directs the user to apply a sample to sample port 10 as the third and last step the user must perform to initiate the measurement sequence. The empty sample port is reflective. When a sample is introduced into the sample port, it absorbs light from LED 46 and thereby reduces the light that is reflected to detector 48. That reduction in light, in turn, signals actuator 42 to release bladder 12. The resultant suction in channel 14 draws sample through the measurement areas to the stop junction. For each measurement area 4, 6 and 8, a LED 50 and detector 52 pair is provided to monitor the light transmitted through the sample as it is clotting.

Analysis of the transmitted light as a function of time (as described below) permits a calculation of the PT time, which is displayed on the meter display 44. Preferably, sample temperature is maintained at about 37° C. by heater 36. Each such function is controlled by a microprocessor chip 54 controlled by software stored in programmable, read-only memory or hard-wired logic 56.

As described above, the detector senses a sample in sample port 10, simply by detecting a reduction in (specular)

reflection of a light signal that is emitted by 46 and detected by 48. However, that simple system cannot easily distinguish between a whole blood sample and some other liquid (e.g., blood serum) placed in the sample port in error or, even, an object (e.g., a finger) that can approach sample port 10 and cause the system to erroneously conclude that a proper sample has been applied.

To avoid this type of error, another embodiment measures diffuse reflection from the sample port. This embodiment appears in FIG. 2B, which shows detector 48 positioned normal to the plane of strip 2. With the arrangement shown here, if a whole blood sample has been applied to sample port 10, the signal detected by 48 increases abruptly, because of scattering in the blood sample, then decreases, because of rouleaux formation. The detector system 32 is thus programmed to require that type of signal before causing actuator 42 to release bladder 12. The delay of several seconds in releasing the bladder does not substantially affect the readings described below.

FIG. 3 depicts a typical "clot signature" curve in which current from detector 50 is plotted as a function of time. Blood is first detected in a measurement area at time 1. In the time interval A, between points 1 and 2, the blood fills the measurement area. The reduction in current during that time interval is due to light scattered by red cells and is thus an approximate measure of the hematocrit. At point 2, sample has filled the measurement area and is at rest, its movement having been stopped by the stop junction. The red cells begin to stack up like coins (rouleaux formation). The rouleaux effect allows increasing light transmission through the sample (and less scattering) in the time interval between points 2 and 3. At point 3, clot formation ends rouleaux formation and transmission through the sample reaches a maximum. The PT time can be calculated from the interval B between points 1 and 3 or between 2 and 3. The result is typically reported in terms of its "INR" (i.e., International Normalized Ratio). Thereafter, the blood changes state from liquid to a semi-solid gel, with a corresponding reduction in light transmission. The reduction in current (C) between the maximum 3 and endpoint 4 correlates with fibrinogen in the sample.

Measurements made on a whole blood sample using the strip yield a curve of the type shown in FIG. 3 for each of the measurement areas. The data from the curves for the controls (measurement areas 6 and 8) are used to qualify the data from the curve for measurement area 4. The measurement of sample from area 4 is validated only when measurements on areas 6 and 8 yield results within a predetermined range. If either or both of these control measurements are outside the range, then a retest with another test strip is indicated. Such an indication would be in order if a test strip is faulty. Ageing or oxidization of reagents can potentially yield failing Control 1 and/or Control 2 tests.

SUMMARY OF THE INVENTION

It has been discovered, however, that in some instances test strip readings outside a typical therapeutic range (2.0 to 8.0 INR) may not be indicative of faulty test strips, but rather due to the characteristics of the test subject's blood. With earlier systems such as that described above which indicate a test strip is faulty and order a retest under such conditions, user compliance would merely result in another error reading, prompting another retest.

The present invention solves a yet heretofore unknown problem with test strip qualification accuracy outside the usual diagnostic or therapeutic range. It may be employed to qualify formerly "false negative" test readings as alluded to above. Correcting such inaccuracy offers benefits in avoiding unwarranted frustration as well as lost time and energy—certainly for the user and possibly that of physicians who might ultimately be consulted. While avoiding such occurrences may indirectly result in economic savings, direct savings may be achieved by the avoidance of erroneously disqualifying a statistically significant number of test strips.

Another improvement optionally offered by the present invention is to disqualify formerly acceptable test strip readings for low INR values. Correcting this inaccuracy and disqualifying former "false positive" offers improved test strip accuracy—a benefit of clear utility. Additional benefits and advantages may also be apparent to those with skill in the art reviewing the subject disclosure.

Systems of the present invention preferably operate in connection with a disposable test strips and hand held meters as described above. Mathematical algorithms or functions, preferably those described in detail below, take assay PT time into account for qualifying PT time results by comparison with results from one or two control-type reactions. Those algorithms as implemented by software and hardware as well as the methodology disclosed form aspects of the present invention.

DETAILED DESCRIPTION OF THE INVENTION

Figure 5:
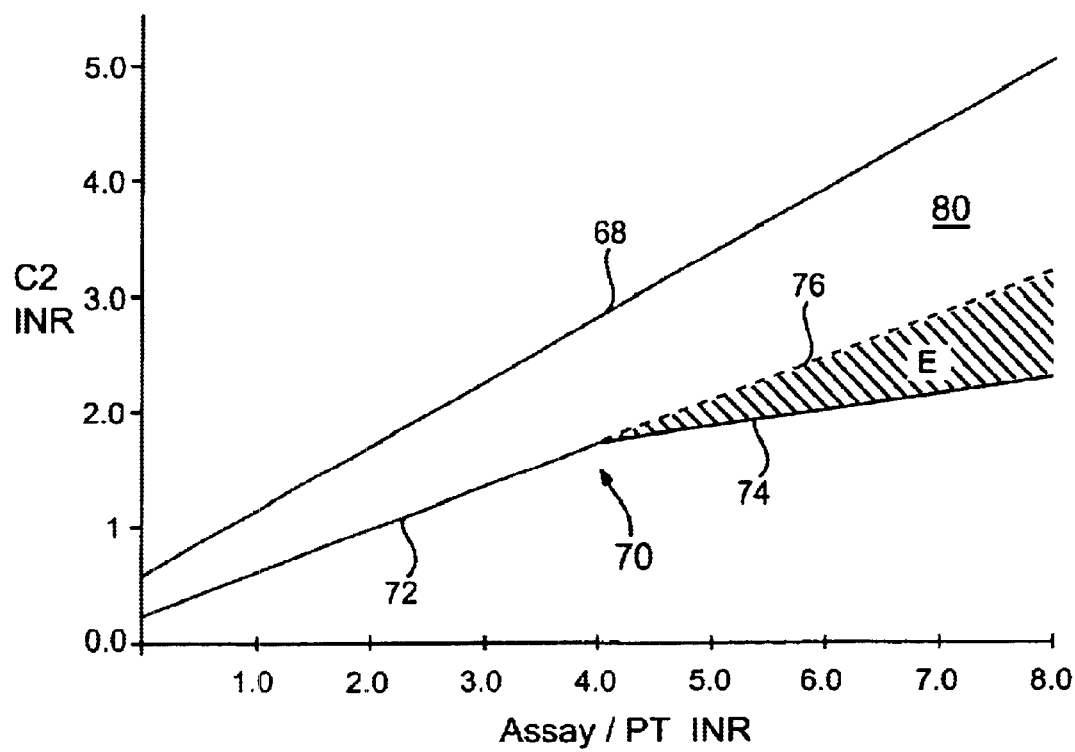

In describing the invention in greater detail than provided in the Summary above, the subject test strip qualification system and methods for its use are described in relation to FIGS. 4 and 5 and various equations. Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims made herein. Furthermore, where a range of values is provided, it is understood that every intervening value, between the upper and lower limit of that range and any other stated or intervening value in that stated range is encompassed within the invention. The upper and lower limits of these smaller ranges may independently be included in the smaller ranges and is also encompassed within the invention, subject to any specifically excluded limit in the stated range. Where the stated range includes one or both of the limits, ranges excluding either both of those included limits are also included in the invention. Also, it is contemplated that any optional feature of the inventive variations described herein may be set forth and claimed independently, or in combination with any one or more of the features described herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are described. All existing subject matter mentioned herein (e.g., publications, patents, patent applications and hardware) is incorporated by reference herein in its entirety. The referenced items are provided solely for their disclosure prior to the filing date of the present application. Nothing herein is to be construed as an admission that the present invention is not entitled to antedate such material by virtue of prior invention.

Also, it is noted that as used herein and in the appended claims, the singular forms "a", "and," "said" and "the" include plural referents unless the context clearly dictates otherwise. Conversely, it is contemplated that the claims may be so-drafted to require singular elements or exclude any optional element indicated to be so here in the text or drawings. This statement is intended to serve as antecedent basis for use of such exclusive terminology as "solely," "only" and the like in connection with the recitation of claim elements or the use of a "negative" claim limitation(s).

Turning now to FIGS. 4 and 5, graphs representing the inventive approaches to test trip qualification are shown. In each graph, subject matter according to the present invention is shown in solid line. Differences between the present approach and another approach, previously developed by LifeScan (Milpitas, Calif.), as described in U.S. Patent Application Ser. No. 10/100,254 titled "Test Strip Qualification System" filed on even date herewith are shown by dashed lines. The differences between each approach are indicated by hatched areas "D" and "E." Still, each approach is preferably practiced in connection with the test strip described in reference to the '840 publication.

In qualifying test strips according to either method, measurements are preferably made on whole blood sample at each of the three test strip measurement areas, yielding curves of the type shown in FIG. 3 used to determine an INR value for each well. First, whole blood sample is drawn into each of the reaction areas so that the fluid rehydrates the dried reagents and reacts at each site. The data obtained for control wells 6 and 8 are used to qualify the data from the curve from measurement area 4 providing PT time. The test results, including that for the controls, is preferably converted to INR results for use in the algorithms described below and reporting results to the user.

Measurement areas 4, 6, and 8 preferably include such compositions as indicated above in connection with the '840 publication where the anticoagulant in sample blood is Coumadin. Of course, which measurement area includes a given composition may be varied, as may the overall test strip configuration. In addition, variation in the reactants themselves is contemplated. Such variation in reactant chemistry would affect the results obtained and precise mathematical relationships described below in a predictably fashion.

As alluded to, for a PT result from the assay measurement to be considered reliable, it must satisfy first and second control conditions ("C1" and "C2" conditions, respectively) by falling within a predetermined result range. FIG. 4 illustrates C1 boundary conditions. Its character is determined by the compounds in reaction area 6 which preferably include recombinant tissue factor with buffers and preservatives, bovine coagulation factors of the extrinsic pathway, and recombinant factor VIIa protein. FIG. 5 illustrates C2 boundary conditions. Its character is determined by the compounds in reaction area 8 which preferably includes recombinant tissue factor with buffers and preservatives and bovine coagulation factors of the extrinsic pathway.

In each figure, the graphs illustrate conditions up to the usual therapeutic value of 8.0 INR. Still, extension of the qualification zone conditions beyond this point is possible. However, qualification for assay PT INR values in a range of 0.8 to 8.0 INR is contemplated. Any result of greater than 8.0 INR is considered and preferably reported as HIGH and any result less than 0.8 INR is considered and preferably reported as LOW.

In FIG. 4, lower limit 58 and upper limit 60 for C1 INR readings are shown. The lower limit is set at about 0.60 INR. This limit is independent of assay INR. However, only a portion of the upper limit is independent of assay INR. At or above an assay INR of about 2.0, the value of the upper limit for C1 INR is about 1.9. For lower assay INR values, a function dependent on assay INR determines the acceptable C1 INR values. For the sake of simplicity and ease of implementation, the function is preferably a line equation. When expressed in the form $y=mx+b$, where y is C1 INR value and x is assay INR value, to best fit test data generated m (the line slope) is ~0.50 and b (the y-intercept) is ~0.91. By use of the "~" sign, it is meant equals or is about equal.

This approach to qualifying PT results with C1 data differs in two significant respects from the Test Strip Qualification System application referenced above. There, if C1 is equal to or between 0.60 and 1.91 INR, the test strip is qualified so far as C1 is concerned. Such an approach is indicated in FIG. 4 where the dashed line 66 continues from line 62. The hatched area D gives an indication of the improvement in test strip qualification accuracy offered by present invention over the previous approach that does not account for assay INR with respect to C1. Test accuracy is improved with respect to C1 by discarding low assay INR results in region D that would otherwise qualify in the above-reference method.

In FIG. 5, upper 68 and lower 70 limits for C2 INR readings are shown. As with a portion of the upper limit in C1, the upper limit 68 for C2 is defined by a function dependent on assay INR value. By testing, C2 INR values have been observed to be proportional to assay INR values. While such a relationship may be expressed in various way, for the sake of simplicity and ease of implementation, the function defining upper limit 68 is preferably a line equation. When expressed in the form $y=mx+b$, where y is C2 INR value, and x is assay INR value, m~0.56 and b~0.60 provide an excellent fit to test data generated.

Lower limit 70 is also defined by a function dependent on assay INR value. It preferably employs two line segments 72 and 74. The first line segment 72 is coincident with the C2 lower limit line in the above-referenced patent application. For each, m~0.36 and b~0.37. However, according to the referenced process, the entire lower limit is dictated by that line. This approach is shown in connection with dashed line segment 76 extending from line segment 72.

In contrast, the present invention qualifies lower value C2 INR readings in instances where the assay INR is at or above about 4.0. A determination of which additional values qualify may be made by comparison to a line segment 74 having a lesser slope, particularly where m~0.15 and b~1.2. As this function diverges from or drops-off from line 72/76, it defines area E that results in the qualification of additional test strips—thus avoiding the problem of "false negatives" described above.

In actuality, the line equations described above may been defined with greater precision. Two significant figures are expressed in order to indicate that variation on such an order is contemplated. Still, FIGS. 4 and 5 are drawn with the precision to which the present invention is preferably practiced. This being said, substantial variability in approach is contemplated as part of the present invention. For instance, one or more polynomial equations may be used to set C1 and C2 bounds. Alternately, tabular data representing results within each qualification range or zone 78 and 80 for C1 and C2, may be employed.

Irrespective of such changes as may be apparent to these with skill in the art, the nature or general approach of the present invention should not change. With respect to C1, the upper limit will take the results of the PT assay into account for lower INR values to disqualify false positives in comparison to the referenced Test Strip Qualification method. With respect to C2, the lower limit will comprise at least two sections, with the second section expanding the qualification zone for a higher INR values as compared to the previous approach.

The methodology of the present invention may be practiced with either one or with both of these improvements. As set forth above, the improvement in FIG. 4 (diagrammatically illustrated by area D) disqualifies formerly erroneously-indicated acceptable results; the improvement in FIG. 5 (diagrammatically illustrated by area E) accepts formerly erroneously-indicated negative results. Practiced together, the improvements of the present invention offer optimal results in terms of economy and accuracy in qualifying test strips.

However the present invention is implemented, in instances where C1 and C2 results are qualified, test strip meter display 44 shows PT time for the assay (preferably in terms of an INR value). If either or both of these control measurements are outside the ranges defined, another sort of message indicating test reliability or fitness is displayed by the test strip meter. Error messages specific to the type of failure may be presented (i.e., messages indicative of C1, C2 or C1 and C2 failure). Alternately, a retest with another test strip may simply be indicated.

Claims

Though the invention has been described in reference to a single illustrated example, optionally incorporating various features, the invention is not to be limited to what is described or indicated as contemplated with respect to possible variation. The breadth of the present invention is to be limited only by the literal or equitable scope of the following claims.

That being said, I claim:

1. A method of test strip qualification, said method comprising:
   providing a test strip comprising an assay reaction area, a first control reaction area and a second control reaction area;
   obtaining prothrombin results for each reaction area;
   comparing results from said first control area to first control qualification criteria and results from said control area to second control qualification criteria, wherein said first control qualification criteria comprise an upper limit and a lower limit, said upper limit being at least partially dependent upon assay reaction area prothrombin results; and
   outputting a message to a user indicating test strip reliability.

2. The method of claim 1, wherein said upper limit is dependent upon assay reaction area prothrombin results at or below about a 2.0 International Normalized Ratio.

3. The method of claim 2, wherein said upper limit comprises a linear function dependent upon assay reaction area prothrombin results.

4. The method of claim 3, wherein said upper limit further comprises a value independent of assay reaction area prothrombin result for assay reaction area prothrombin results at or above about a 2.0 International Normalized Ratio.

5. The method of claim 3, wherein said lower limit comprises a value independent of assay reaction prothrombin result.

6. The method of claim 1, wherein prothrombin results obtained for each reaction area are International Normalized Ratio values.

7. The method of claim 1, wherein said second control qualification criteria comprises an upper limit and a lower limit, said upper limit being dependent upon assay reaction area prothrombin results, said lower limit having first and second sections dependent upon assay reaction area prothrombin results, wherein said second section drops-off from said first section.

8. A method of test strip qualification, said method comprising:
   providing a test strip comprising an assay reaction area, a first control reaction area and a second control reaction area;
   obtaining prothrombin results for each reaction area;
   comparing results from said first control area to first control qualification criteria and results from said second control area to second control qualification criteria, wherein said second control qualification criteria comprise an upper limit and a lower limit, said upper limit being dependent upon assay reaction area prothrombin results, said lower limit having first and second sections dependent upon assay reaction area prothrombin results, wherein said second section drops-off from said first section; and
   outputting a message to a user indicating test strip reliability.

9. The method of claim 8, wherein said lower limit first and second sections comprise linear functions.

10. The method of claim 8, wherein said first section and said second section coincide at an assay reaction area prothrombin result of about a 4.0 International Normalized Ratio.

11. The method of claim 8, wherein said upper limit comprises a linear function.

12. The method of claim 8, wherein prothrombin results obtained for each reaction area are International Normalized Ratio values.

13. The method of claim 8, wherein said first control qualification criteria comprises an upper limit and a lower limit, said upper limit being at least partially dependent upon assay reaction area prothrombin results.

14. A system programmed to operate according to a method selected from a group of methods consisting of the test strip qualification methods of claims 1–13.

15. The system of claim 14, further comprising a test strip comprising an assay reaction area, a first control reaction area and a second control reaction area.

16. A computer-readable medium embodying a program to direct a system to perform a method selected from a group of methods consisting of the test strip qualification methods of claims 1–13.

17. A computer-readable medium containing data representing sample results, wherein said data is made by a method selected from a group of methods consisting of the test strip qualification methods of claims 1–13.

* * * * *